(12) United States Patent
Schnabel et al.

(10) Patent No.: US 7,083,925 B2
(45) Date of Patent: Aug. 1, 2006

(54) **METHOD OF PARENTAGE TESTING IN NORTH AMERICAN BISON, *BISON BISON* AND DOMESTIC CATTLE USING MICROSATELLITE LOCI**

(76) Inventors: Robert D. Schnabel, 2013 Sunborough, Columbia, MO (US) 65203; James N. Derr, 5781 Blue Ridge Dr., College Station, TX (US) 77845

(*) Notice: Subject to any disclaimer, the term of this patent is extended or adjusted under 35 U.S.C. 154(b) by 599 days.

(21) Appl. No.: 10/340,939

(22) Filed: Jan. 13, 2003

(65) Prior Publication Data

US 2003/0170701 A1 Sep. 11, 2003

Related U.S. Application Data

(60) Provisional application No. 60/347,792, filed on Jan. 11, 2002.

(51) Int. Cl.
*C12Q 1/68* (2006.01)
*C12P 19/34* (2006.01)

(52) U.S. Cl. .......................................... 435/6; 435/91.2
(58) Field of Classification Search ...................... None
See application file for complete search history.

(56) References Cited

OTHER PUBLICATIONS

Cattle Diversity Database, http://www.projects.roslin.ac.uk/cdiv/.*
Parentage Testing Committee, American Association of Blood Banks (1998) Standards for Parentage Testing Laboratories, American Association of Blood Banks, Bethesda, MD.*
Glowatzki-Mullis ML, Gaillard C, Wigger G, Fries R. Microsatellite-based parentage control in cattle. Anim Genet. Feb. 1995;26(1):7-12.*
Heyen DW, Beever JE, Da Y, Evert RE, Green C, Bates SR, Ziegle JS, Lewin HA. Exclusion probabilities of 22 bovine microsatellite markers in fluorescent multiplexes for semiautomated parentage testing. Anim Genet. Feb. 1997;28(1):21-7.*
Mommens G, Van Zeveren A, Peelman LJ. Effectiveness of bovine microsatellites in resolving paternity cases in American bison, Bison bison L. Anim Genet. Feb. 1998;29(1):12-8.*
Neff BD, Repka J, Gross MR. Statistical confidence in parentage analysis with incomplete sampling: how many loci and offspring are needed? Mol Ecol. May 2000;9(5):529-39.*

Webster MS, Reichart L. Use of microsatellites for parentage and kinship analyses in animals. Methods Enzymol. 2005;395:222-38.*
Bishop MD, Kappes SM, Keele JW, Stone RT, Sunden SL, Hawkins GA, Toldo SS, Fries R, Grosz MD, Yoo J, et al. A genetic linkage map for cattle.□□Genetics. Feb. 1994;136(2):619-39.*
Stone RT, Pulido JC, Duyk GM, Kappes SM, Keele JW, Beattie CW. A small-insert bovine genomic library highly enriched for microsatellite repeat sequences. Mamm Genome. Oct. 1995;6(10):714-24.*
Stone RT, Kappes SM, Keele JW, Beattie CW. Characterization of 109 bovine microsatellites. Anim Genet. Feb. 1997;28(1):62-6.*
Sunden SL, Stone RT, Bishop MD, Kappes SM, Keele JW, Beattie CW. A highly polymorphic bovine microsatellite locus: BM2113. Anim Genet. Feb. 1993;24(1):69.*
McGraw RA, Grosse WM, Kappes SM, Beattie CW, Stone RT. Thirty-four bovine microsatellite markers. Anim Genet. Feb. 1997;28(1):66-8.*
Ihara N, et al A comprehensive genetic map of the cattle genome based on 3802 microsatellites. Genome Res. Oct. 2004;14(10A):1987-98.*
Validation of 15 microsatellites for parentage testing in North American bison, Bison bison and domestic cattle by R.D. Schnabel, T.J. Ward, and J.N. Derr. Animal Genetics 2000, 31, 360-366.

* cited by examiner

*Primary Examiner*—Juliet C. Switzer
*Assistant Examiner*—Stephen Kapushoc
(74) *Attorney, Agent, or Firm*—Brouse McDowell; Heather M. Barnes

(57) ABSTRACT

A method for determining parentage of North American bison or domestic cattle offspring. In the method an offspring is tested to determine the alleles present in that offspring for selected loci. A pool of potential parents is also tested to determine which alleles of these loci are present in each parent. The likelihood that any potential parent is the parent of the offspring may then be determined by looking for the presence or absence of an allele in the offspring that is present in the parent or by some comparable method. The method may also be used to exclude all potential parents in a pool. Sixteen loci which may be used in such an analysis are BM1225, BM1706, BM17132, BM1905, BM2113, BM4440, BM720, BMS1862, BMS410, BMS510, BMS527, RM372, BMS1172, BMS2639, BM3628 and BMS2325. The method used to select these loci is also disclosed.

2 Claims, No Drawings

METHOD OF PARENTAGE TESTING IN NORTH AMERICAN BISON, *BISON BISON* AND DOMESTIC CATTLE USING MICROSATELLITE LOCI

This application claims priority from a provisional application filed on Jan. 11, 2002, having Ser. No. 60/347,792, which is incorporated herein by reference.

This invention was made with Government support under 'Validation of 15 Microsatellites for Parentage Testing is North America', NSF Grant No. DEB-9622126, 'Identification of Domestic Cattle Hybrids in Wild Cattle', NSF Grant No. DEB-9622126, and 'Nuclear Gene Marker for Cattle', NSF Grant No. DEB-9622126 awarded by the National Science Foundation. The Government has certain rights in this invention.

BACKGROUND OF THE INVENTION

The present invention relates to a method of determining parentage in bison and domestic cattle using distinct microsatellite loci.

Bison once numbered in the millions in North America but due to the population bottleneck experienced in the late 1800's, bison numbers were reduced to no more than 300 individuals by 1880 (Coder 1975; Dary 1989). Almost all of the bison alive today can be traced back to five populations that were used to repopulate most of the extant public and private herds (Coder 1975). Current semi-wild bison populations are fragmented among public parks and sanctuaries throughout the United States and Canada. However, the vast majority of bison today reside on private ranches where they are raised for meat production. Recently, Mommens et al. (1998) demonstrated that bovine microsatellites are better suited for parentage testing in bison than conventional blood typing due to a greater degree of variation. However, their sample was limited to a single herd located in Belgium, which probably does not represent the actual genetic variation found in bison in North America.

Currently, parentage testing in domestic animals is based on exclusionary techniques using genetic markers. An offspring is tested assuming one known parent and one or a limited number of candidate parents. If only one candidate parent is left non-excluded, that parent is assigned parentage to the offspring. Although one non-excluded parent may be the true parent, there exists the possibility that other non-excluded candidate parents exist in the population but were not considered. A likelihood based testing procedure is more appropriate for situations in which there are many candidate parents and obtaining a known parent is difficult. Using likelihood based procedures, all potential parents are considered as candidates and there is no need to identify a known parent prior to testing.

SUMMARY OF THE INVENTION

The purpose of this study was to characterize, standardize and provide validation for a set of highly polymorphic microsatellites for use in routine parentage testing in North American Bison and domestic cattle.

Fifteen bovine microsatellites were evaluated for use in parentage testing in 725 bison from 14 public populations, 178 bison from two private ranches and 107 domestic cattle from 5 different breeds. The number of alleles per locus ranged from 5 to 16 in bison and from 5 to 13 in cattle. On average, expected heterozygosity, polymorphism information content (PIC) and probability of exclusion values were slightly lower in bison than in cattle. A core set of 12 loci was further refined to produce a set of multiplexed markers suitable for routine parentage testing. Assuming one known parent, the core set of markers provides exclusion probabilities in bison of 0.9955 and in cattle of 0.9995 averaged across all populations or breeds tested. Tests of Hardy-Weinberg and linkage equilibrium showed only minor deviations. This core set of 12 loci represent a powerful and efficient method for determining parentage in North American bison and domestic cattle.

Further tests have also indicated that two additional loci of the 15 originally identified, BMS1172 and BMS2639, may also be suitable for parentage testing. Two other loci, BM3628 and BMS2325, have subsequently been identified as suitable loci through testing in the two private bison herds.

The above summary provides a general outline of the invention. For a better understanding of the invention and its advantages, reference may be made to the following description of exemplary embodiments.

DETAILED DESCRIPTION OF THE INVENTION

The present invention includes a method of determining parentage in bison or domestic cattle using microsatellite loci. These loci were selected as set forth below and may be used in any type of parentage testing in which allelic variation is used to determine the likelihood of parentage. Preferred methods of detecting the specific alleles in the offspring and potential parents are described below, but alternative methods may also be employed. When used with the methods described below, the indicated levels of certainty are achieved. Alternative methods may result in differences of certainty if the methods change the probability that allele assignments are correct. One skilled in the art will be able to select alternative methods of detecting specific alleles which result in a desired level of overall parentage certainly.

In a preferred embodiment, 12 loci, BM1225, BM1706, BM17132, BM1905, BM2113, BM4440, BM720, BMS1862, BMS410, BMS510, BMS527, RM372, are used. However, one skilled in the art will understand that paternity may be determined using only a subset of these loci. The full set or any subset may also be used with any other loci useful in determining parentage. The four additional loci later identified as acceptable for parentage testing, BMS1172, BMS2639, BM3628 and BMS2325, may also be used in testing. Based upon known or readily determinable allele types and frequencies in a given population for each loci, a set of loci comprising the above loci and/or any other known loci may be selected for parentage testing. In general, the more loci selected, the greater the certainty of any parentage assignment will be. However, the invention by no means requires the use of all of the 12 loci originally identified, not does it require that a total of 12 loci be used in every embodiment. In a preferred embodiment, at least two loci are selected from the 16 identified above.

The goal of the study leading to the present invention was to characterize, standardize and provide validation for a set of polymorphic microsatellites for use in routine parentage testing in North American bison and domestic cattle. Table 3 demonstrates that the exclusion probabilities found in bison and cattle for these loci are comparable to other loci previously described (Glowatzki-Mullis et al. 1995; Peelman et al. 1998; Heyen et al. 1997; Mommens et al. 1998). Additionally, in cattle the core set of markers produces similar exclusion probabilities to the commercially available StockMarks™ kit (PE Biosystems). However, in bison the core set of markers offer higher exclusion probabilities than either the StockMarks™ kit or the ISAG approved set of markers (Mommens et al. 1998).

In order to validate the use of these markers for parentage testing in bison, the guidelines set forth for selecting loci for human parentage testing were followed (Parentage Testing Committee, American Association of Blood Banks, 1997). A total of 121 offspring were tested from two separate private populations. In every case the loci exhibited normal co-dominant Mendelian inheritance with no evidence of null alleles or mutaions. Similar validation studies were conducted using the BM3628 and BMS2325 loci similar results.

The development of an allelic ladder, which is used for each genotyping run, fulfills the requirement of a known DNA control and makes it possible to directly compare samples that are run at different points in time or even on different machines. In the case of parentage testing of domestic animals, this is a desirable feature since offspring will be tested years apart and re-running parents each year would be inefficient and costly. An allelic ladder also increases consistency between laboratories since each genotype is assigned relative to a known standard. Locus BMS510 exhibited single base pair differences in bison. Normally this would preclude this locus from being used as a marker for parentage testing due to the difficulty in allele assignment reproducibility. However, this problem was overcome by sizing alleles relative to the allelic ladder. The minimum and maximum standard deviation of allele sizes for this locus was 0.06 and 0.25 bp respectively with an average over all the alleles of 0.09 bp. These values represent between gel deviations. The within gel standard deviation, averaged across alleles, is reduced to only 0.06 bp. Smith (1995) demonstrated that values in this range were highly unlikely to produce incorrect allele assignment when an allelic ladder is used.

In order to use allele frequencies to calculate genotype frequencies and exclusion probabilities, allele frequencies from the populations tested must be consistent with HW expectations. 903 bison from 14 public populations and two private populations represent an adequate sample with which to estimate allele frequencies. Tests of HWE, although showing minor deviations for some locus population combinations, did not yield consistent deviations for the testing methods employed. The number of HW deviations observed in this study is similar to other studies in humans. Hammond et al. (1994) found 11.5% (18/156), Edwards et al. (1992) found 11.6% (7/60) and Thomson et al. (1999) found 5.5% (2/36) of the possible locus-population-test combinations showed deviations, which is comparable to the 7.5% (71/942) found in the current study. The lack of consistency in the observed deviations leads us to conclude that these loci are in HWE for the populations tested.

Tests of genotypic disequillibrium showed no consistent deviations in the populations which were not expected a priori to show deviations. In a production setting such as with the HHP and ABR populations, genotypic disequillibrium is expected because a limited number of bulls are used for breeding. However, in these cases typically the entire population will be tested and departures from genotypic equilibrium will have little effect on the final parentage analysis. Therefore, we conclude that the observed deviations in HWE and genotypic equilibrium are small enough that they will not significantly affect the calculations of genotypic frequencies or multilocus probabilities from allele frequencies.

The advantages of likelihood based parentage assignment over exclusionary methods have been demonstrated by Slate et al. (2000) for natural populations and extended to captive production populations in the current study. Indeed, even with highly developed sets of markers such as those presented here, genotyping errors occur. A likelihood-based system to assign parentage allows the lab to identify potential errors or mutations and make corrections before parentage is rejected.

PCR based methods in conjunction with highly variable microsatellite loci and fluorescent based genotyping provide the technologies needed to establish a new standard for parentage testing. The core set of 12 microsatellites presented here along with 4 additional microsatellites offers a powerful battery of markers for both parentage testing and individual identification. These loci are preferably used as the core set of 12 or in combination with one or more of the 4 additional loci, but they may be combined in whole or in part with other loci without substantial loss of identification power. These markers when used in likelihood based parentage testing will help to refine breeding programs and allow for improved genetic management by accurate determination of pedigrees in both bison and cattle.

The invention may be better understood through reference to the specific examples which follow. Although only preferred embodiments of the invention are specifically described above and in the examples, it will be appreciated that modifications and variations of the invention are possible without departing from the spirit and intended scope of the invention.

EXAMPLES

Example 1

DNA Source

Fourteen public bison herds, two private bison herds and five cattle breeds were sampled. Sample sizes and population locations are listed in Table 1. These herds represent most of the major public herds that have played a role in populating private bison herds around the world. Therefore, the majority of the genetic variation present in extant bison herds should be contained within these public herds.

TABLE 1

Bison populations and domestic cattle breeds sampled.

| Public Herds | Abbreviation | Location | Sample Size |
|---|---|---|---|
| Antelope Island State Park | AI | Utah | 67 |
| Custer State Park | CSP | South Dakota | 37 |
| Elk Island National Park (woods) | EIW | Alberta | 25 |
| Elk Island National Park (plains) | EIP | Alberta | 24 |
| Fort Niobrara National Wildlife Refuge | FN | Nebraska | 24 |
| Finney Game Refuge | GC | Kansas | 50 |
| Henry Mountains | HM | Utah | 21 |
| Caprock Canyon State Park | CCSP | Texas | 33 |
| Mackenzei Bison Sanctuary (woods) | MBS | Canada | 40 |
| Maxwell Game Refuge | MX | Kansas | 35 |
| National Bison Range | NBR | Montana | 38 |
| Wind Cave National Park | WC | South Dakota | 152 |
| Wood Buffalo National Park (woods) | WBNP | Canada | 21 |
| Yellowstone National Park | YNP | Wyoming | 158 |
| | | Total | 725 |
| Private Herds | | | |
| Arrowhead Buffalo Ranch, Ltd. | ABR | Ohio | 135 |
| Hidden Hollow Preserve | HHP | Kentucky | 43 |
| | | Total | 178 |
| Cattle Breeds | | | |
| Angus | AN | | 54 |
| Hereford | HE | | 16 |
| Holstein | HO | | 12 |

TABLE 1-continued

Bison populations and domestic cattle breeds sampled.

| Public Herds | Abbreviation Location | Sample Size |
|---|---|---|
| Shorthorn | SH | 12 |
| Texas Longhorn | TLH | 13 |
| | Total | 107 |

Example 2

DNA Extraction

Genomic DNA was isolated from white blood cells by proteinase K treatment followed by phenol chloroform extraction (Sambrook et al. 1989) or by using the SUPER QUICK-GENE DNA Isolation kit (Analytical Genetic Testing Center, Inc. Denver, Colo.). DNA was also extracted from hair follicles using the following procedure. Approximately 8–12 hair follicles were cut from the switch of the tail using a razor blade and digested for four hours at 55° C. in 200 µl lysis buffer (500 mM KCl, 100 mM Tris-HCl pH 8.0, 0.1 µg/ml gelatin, 0.45% Triton X-100, 0.45% Tween-20, 0.5 mg/ml proteinase K). After digestion, samples were centrifuged at 5,000 g for two minutes. The clear aqueous layer was then transferred to a new tube and 0.5 µl of 10 mg/ml RNase A was added. The sample was then extracted once with phenol/chloroform/isoamyl alcohol (25:24:1) followed by a chloroform extraction. DNA was ethanol precipitated then resuspended in 50 µl TE buffer (10 mM Tris-HCl, 1 mM EDTA pH 8.0).

Example 3

Loci

Bovine microsatellites were chosen from the USDA cattle mapping database (sol.marc.usda.gov) that fulfilled the following set of criteria in cattle:
1. High PIC values, high heterozygosity and a large number of alleles
2. Lack of known null alleles
3. Loci non-syntenic or separated by more than 40 cM
4. Allele size range
5. Suitability for multiplex PCR.

Primer sequences flanking 15 microsatellites that fulfilled these criteria were synthesized with a fluorescent label attached to the 5' end of each forward primer (Table 2).

TABLE 2

Chromosomal location and fluorescent dye used for each of the 15 loci selected from the USDA database.

| Locus | Chr.[a] | Pos.[a] | Dye[b] |
|---|---|---|---|
| BM1225 | 20 | 8.0 | TET |
| BM1706 | 16 | 80.6 | 6FAM |
| BM17132 | 19 | 58.6 | 6FAM |
| BM1905 | 23 | 64.3 | TET |
| BM2113 | 2 | 106.2 | 6FAM |
| BM4440 | 2 | 55.0 | TET |
| BM720 | 13 | 38.6 | TET |
| BMS1117 | 21 | 9.9 | HEX |
| BMS1172 | 4 | 27.3 | 6FAM |
| BMS1862 | 24 | 32.8 | HEX |
| BMS2639 | 18 | 57.0 | 6FAM |
| BMS410 | 12 | 0.0 | TET |
| BMS510 | 28 | 22.1 | HEX |
| BMS527 | 1 | 55.9 | 6FAM |
| RM372 | 8 | 19.1 | HEX |

[a]Bovine chromosome and relative position (cM).
[b]ABI fluorescent label used with forward primer.

Example 4

Multiplex PCR

Based on the results of genotyping approximately 500 bison and 50 cattle for these 15 loci, a core set of 12 loci were selected which could be amplified in two PCR reactions and co-loaded in a single lane of an ABI Prism377 sequencer or a single injection on an ABI Prism 310 capillary-based genetic analyzer. Core multiplex A consists of BMS510, BMS410, BM17132, RM372 and BMS527. Core multiplex B consists of BM4440, BM2113, BMS1862, BM1905, BM720, BM1706 and BM1225. PCR conditions for core multiplexes A and B are as follows: 25–100 ng template DNA, 10 mM Tris-HCl (pH 9.0), 50 mM KCl, 1% Triton®-X, 3.0 mM $MgCl_2$, 500 µm dNTPs, 0.05–0.3 µm each primer, 1X MasterAmp PCR enhancer (Epicentre Technologies), and 0.5U Taq DNA polymerase (Promega) in a 5 µl reaction. Thermal cycle parameters for core multiplex A and B were 2 minutes 96° C. followed by 35 cycles of (15 seconds 96° C., 15 seconds 54° C., 5 seconds 72° C.) with a final extension step of 20 minutes at 72° C. using a GeneAmp® PCR 9700 thermocycler (PE Biosystems). In later experiments a total of 16 loci, including the BMS1172, BMS2639, BM3628 and BMS2325 were amplified.

Example 5

Genotyping

PCR products were separated on an ABI Prism 377 DNA Sequencer (ABI377) or an ABI Prism 310 Genetic Analyzer (ABI310)(PE Biosystems) and sized relative to an internal size standard (GS500, PE Biosystems or MAPMARKER LOW, Bioventures). Fluorescent signals from the dye labeled microsatellites were detected using GENESCAN 3.1 software (PE Biosystems). Genotypes were assigned using Genotyper 2.0 software (PE Biosystems) by assigning both an integer value and the actual decimal value (called size) to each peak. After the allelic ladder was developed, the ladder was included on each gel (ABI377) or with each group of samples (ABI310) and genotypes were assigned relative to the actual sequence sizes of the allelic ladder. Previous samples that were genotyped without the allelic ladder were re-assigned genotypes based on the true sequence size of each allele.

Example 6

Cloning and Sequencing

Approximately one half of the bison alleles at each locus were cloned and sequenced. Samples were amplified individually and cloned using either the Original TA Cloning Kit or the Topo TA Cloning kit (Invitrogen) as per the manufacturer's protocol. Approximately 10–20 positive clones from each ligation were picked and grown overnight in 3 ml Terrific Broth containing 50 µg/ml ampicilin. A standard alkali-lysis mini-prep procedure was used to recover plasmid DNA (Sambrook et al. 1989). Plasmid DNA was diluted 1:50 with TE buffer and used as a source of template DNA for PCR. Each positive clone was amplified via PCR and genotyped using the ABI310. Clones that sized identical to one of the original alleles of the animal were used to make glycerol stocks. Cloned alleles were sequenced using the Big-dye™ terminator cycle sequencing kit (PE Biosystems) and an ABI377 automated sequencer. Sequenced alleles were submitted to Genbank and have accession numbers AF213181 to AF213246. An allelic ladder was constructed by mixing equimolar amounts of DNA from the sequenced plasmids into a DNA mastermix. The combined plasmids were used as template DNA for the allelic ladder in each PCR multiplex.

Example 7

Data Analysis

Expected heterozygosity (Nei, 1987), exclusion probabilities and polymorphism information content (PIC) (Botstein et al, 1980) were calculated for each marker within each population. Two exclusion probabilities were calculated which correspond to different scenarios. Exclusion probability one (PE1) assumes genotypes are known for the offspring and a putative parent, but genotypes are not available for a known parent (one parent missing). Exclusion probability two (PE2) assumes genotypes are known for the offspring, one confirmed parent, and one putative parent (both parents genotyped). PE1 and PE2, as well as combined exclusion probabilities were calculated according to Jamieson & Taylor (1997). Tests of Hardy-Weinberg equilibrium (HWE) were performed using the program GENEPOP version 3.1d (Raymond and Rousset, 1995). Exact p-values were calculated for loci that had four alleles or less in a population. For loci that had more than four alleles present in a population, an unbiased estimate of the exact HW probability was calculated using the Markov chain method of Guo and Thompson (1992). Unbiased estimates of genotypic disequilibrium were calculated with GENEPOP using the Markov chain method. Parameters used for all Markov chain procedures were dememorization of 10,000 steps, 125 batches and 40,000 iterations per batch for a total Markov chain length of 5 million steps.

Example 8

Parentage Inference

Parentage testing was performed on the two pedigreed private bison herds to evaluate the actual effectiveness of the loci for determining parentage, verify Mendelian inheritance and check for the presence of null alleles. The accuracy of these pedigrees have previously been verified by genotyping over 200 microsatellites in these herds (unpublished data). The ABR sample contained 92 offspring and 44 potential parents. The HHP sample contained 29 offspring and 22 potential parents. Likelihood based parentage testing was performed using the program CERVUS 1.0 (Marshall et al., 1998) following the procedures outlined in the program. Analysis parameters used for simulations were as follows: 10,000 cycles, 45 candidate parents for the ABR herd and 22 candidate parents for the HHP herd, 95% of the candidate parents sampled, 100% of the loci typed, 1% typing error, 80% relaxed confidence and 95% strict confidence.

Unbiased expected heterozygosity, PIC, exclusion probabilities, allele frequencies, repeat length and the standard deviation in allele size calling are located in Table 4 and can be obtained via the internet at www.cvm.tamu.edu/derrlab/index.html. A total of 138 and 151 alleles were found in bison and domestic cattle respectively. The number of alleles per locus ranged from 5 to 16 in bison and from 5 to 13 in cattle. Of the 15 loci tested, 5 had a greater number of alleles in bison than in domestic cattle. For four of these loci, BM2113, BM1706, BMS1172 and BMS2639, this result is probably due to the limited number of cattle tested. According to published results, all four of these loci have an equal number of alleles or more in cattle compared to what was observed in bison (Stone et al. 1995; Bishop et al. 1994). The exception is BM1225 in which 16 alleles were observed in bison but cattle are reported to only have 11 alleles. Excluding BM4440 for the CCSP population, which was monomorphic, expected heterozygosities in bison ranged from 84.2% to 6.0% and from 85.4% to 39.8% for cattle. The overall mean heterozygosity across all populations and all markers was 62.17% for bison and 70.16% for cattle (Table 3). The only populations that failed to reach the 99% threshold for PE2 were Antelope Island and the CCSP population. This is most likely due to the fact that both of these herds were founded by a small number of individuals and have remained genetically isolated for much of their history (Coder 1975; Popov and Low 1950).

TABLE 3

Mean expected heterozygosity across all 15 loci and combined average exclusion probabilities for all 15 loci and the core set of 12 loci.

| Population | Mean Expected Heterozygosity | All Loci | | Core Set | |
|---|---|---|---|---|---|
| | | PE1 | PE2 | PE1 | PE2 |
| AI | 0.4496 | 0.8622 | 0.9858 | 0.8612 | 0.9820 |
| CSP | 0.6818 | 0.9953 | 0.9999 | 0.9901 | 0.9997 |
| EIP | 0.6666 | 0.9938 | 0.9999 | 0.9894 | 0.9997 |
| EIW | 0.5541 | 0.9663 | 0.9989 | 0.9506 | 0.9974 |
| FN | 0.6602 | 0.9943 | 0.9999 | 0.9860 | 0.9996 |
| GC | 0.6521 | 0.9923 | 0.9999 | 0.9828 | 0.9994 |
| HM | 0.5757 | 0.9777 | 0.9991 | 0.9599 | 0.9973 |
| CCSP | 0.4160 | 0.8457 | 0.9796 | 0.7768 | 0.9570 |
| MBS | 0.6334 | 0.9893 | 0.9998 | 0.9838 | 0.9996 |
| MX | 0.6729 | 0.9956 | 0.9999 | 0.9916 | 0.9998 |
| NBR | 0.6542 | 0.9902 | 0.9998 | 0.9714 | 0.9988 |
| WBNP | 0.6759 | 0.9950 | 0.9999 | 0.9886 | 0.9997 |
| WC | 0.6630 | 0.9943 | 0.9999 | 0.9859 | 0.9995 |
| YNP | 0.6340 | 0.9898 | 0.9998 | 0.9813 | 0.9993 |
| ABR | 0.6981 | 0.9972 | 1.0000 | 0.9920 | 0.9998 |
| HHP | 0.6591 | 0.9956 | 0.9999 | 0.9920 | 0.9995 |
| AN | 0.6907 | 0.9965 | 1.0000 | 0.9934 | 0.9999 |
| HE | 0.6359 | 0.9839 | 0.9995 | 0.9662 | 0.9981 |
| HO | 0.7279 | 0.9978 | 1.0000 | 0.9930 | 0.9999 |
| SH | 0.7029 | 0.9971 | 1.0000 | 0.9930 | 0.9999 |
| TLH | 0.7507 | 0.9993 | 1.0000 | 0.9984 | 1.0000 |
| Mean Bison | 0.6217 | 0.9734 | 0.9976 | 0.9610 | 0.9955 |
| Mean Cattle | 0.7016 | 0.9949 | 0.9999 | 0.9888 | 0.9995 |

Example 9

Hardy-Weinberg & Genotypic Disequilibrium Tests

Calculation of genotype frequencies and exclusion probabilities from allele frequencies depend on the underlying assumptions of HWE. However, the errors associated with using allele frequencies to calculate genotype frequencies and exclusion probabilities should be minimal as long as there is approximate agreement with HW expectations.

In order to test Hardy-Weinberg assumptions, three distinct tests of HWE were performed with the difference being the alternate hypothesis to equilibrium. Each locus within each population was checked for HWE for a total of 314 comparisons (CCSP was monomorphic at BM4440). Eight percent (25/314) of the locus/population combinations showed significant departure from HWE at $p<0.05$ for the probability test. In order to more precisely identify these deviations, score tests (U-tests) (Rousset and Raymond 1995) were performed with the alternative hypothesis of either heterozygote excess or deficiency. When the alternative hypothesis was heterozygote excess, 4.1% (13/314) of the locus/population combinations showed significant deviations from HWE at p<0.05. When the alternative hypothesis was heterozygote deficiency 10.5% (33/314) of the locus/population combinations were significant at p<0.05. There was no consistency between the three tests to indicate any specific locus/population was in disequilibrium.

Non-random association of gametes to form genotypes could also affect using allele frequencies to calculate genotype frequencies. In natural populations this is most likely due to population sub-structuring. Tests of genotypic disequilibrium within populations resulted in 1876 comparisons. Three populations (Al, ABR and HHP) were not tested for genotypic disequilibrium since all three of these populations use a limited number of breeding bulls. When these populations were eliminated from consideration because of known breeding structure, 6.4% (120/1876) of the combinations were significant at p<0.05. Tests of genotypic disequilibrium across populations resulted in 105 comparisons. No locus pairs showed significant disequilibrium across populations at p<0.05 (Bonferoni corrected).

Example 10

Parentage Inference

Both the ABR and HHP pedigrees were used to check the inheritance of the markers and to evaluate the effectiveness of both the markers and the likelihood testing procedure in a production setting. A total of 121 offspring were used to evaluate the test's effectiveness. For each offspring, every reproductively capable animal in the population was considered as a potential parent, allowing for the possibility of missing parents. The first cycle of parentage analysis resulted in eliminating all potential parents that showed incompatibilities at more than one locus. Parents that showed mismatches at one locus were considered as potential parents to allow for the possibility of either a mutation or a genotyping error. The potential parents that were left were then considered as known parents and this additional information was used to re-test the offspring against the original set of potential parents. After the second round of parentage analysis in the ABR herd, 87% (80/92) of the offspring were unambiguously assigned parentage to the correct sire and dam. A total of 12 offspring were not assigned parentage after the second cycle because these 12 cows were purchased as bred heifers; therefore the sires were unavailable. After inspecting the results from the first cycle of parentage analysis, the correct dam was assigned with >95% confidence in each case where the sire was unavailable. Parentage analysis results for the HHP population were much the same as for ABR. Every offspring was unambiguously assigned parentage except two offspring whose sire was not sampled, in which case, the correct dam was assigned with >95% confidence.

REFERENCES

The following references are incorporated by reference herein.

Bishop M. D., Kappes S. M., Keele J. W., Stone R. T., Sunden S. L. F., Hawkins G. A., Toldo S. S., Fries R., Grosz M. D., Yoo J., & Beattie C. W. (1994) A genetic linkage map for cattle. *Genetics* 136, 619–639.

Botstein D., White R. L., Skolnick M. & Davis R. W. (1980) Construction of a genetic linkage map in man using restriction fragment length polymorphisms. *American Journal of Human Genetics* 32, 314–31.

Coder G. D. (1975) The national movement to preserve the American buffalo in the United States and Canada between 1880 and 1920. Ph.D. dissertation, The Ohio State University.

Dary D. A. (1989) The buffalo book. The Swallow Press Inc., Chicago.

Edwards A., Hammond H. A., Jin L., Caskey C. T., & Chakraborty R. (1992) Genetic variation at five trimeric and tetrameric tandem repeat loci in four human population groups. *Genomics* 12, 241–253.

Glowatzki-Mullis M-L., Gaillard C., Wigger G., & Fries R. (1995) Microsatellite-based parentage control in cattle. *Animal Genetics* 26, 7–12.

Guo S. W. and Thompson E. A. (1992) Performing the exact test of Hardy-Weinberg proportions for multiple alleles. *Biometrics* 48, 361–372. Sambrook Fritsch and Maniatas (1989)

Hammond H. A.,Jin L., Zhong Y., Caskey C. T., & Chakraborty R. (1994) Evaluation of 13 short tandem repeat loci for use in personal identification applications. *Am. J. Hum. Genet.* 55, 175–189.

Heyen D. W., Beever J. E., Da Y., Everet R. E., Green C., Bates S. R. E., Ziegle J. S., & Lewin H. A. (1997) Exclusion probabilities of 22 bovine microsatellite markers in fluorescent multiplexes for semi-automated parentage testing. *Animal Genetics* 28, 21–27.

Jamieson A. and Taylor St. C. S. (1997) Comparison of three probability formulae for parentage exclusion. *Animal Genetics* 28, 397–400.

Marshall T. C., Slate J., Bruuk L. E. B., & Pemberton J. M. (1998) Statistical confidence for likelihood-based paternity inference in natural populations. *Molecular Ecology* 7, 639–655.

Mommens G., Van Zeveren A., and Peelman L. J. (1998) Effectiveness of bovine microsatellites in resolving paternity cases in American bison, *Bison bison* L. *Animal Genetics* 29, 12–18.

Nei M. (1987) Molecular Evolutionary Genetics. Columbia University Press. New York.

Parentage Testing Committee, American Association of Blood Banks (1997) *Standards for Parentage Testing Laboratories*, American Association of Blood Banks, Bethesda, Md.

Peelman L. J., Mortiaux F., Van Zeveren A., Dansercoer A., Mornmens G., Coopman F., Bouquet Y., Burny A., Renaville R., & Portetelle D. (1998) Evaluation of genetic variability of 23 bovine microsatellite markers in four Belgian cattle breeds. *Animal Genetics* 29, 161–167.

Popov B. H. and Low J. B. (1950) Game, fur animal and fish, Introductions into Utah. Miscellaneous Publication No.4 of the Utah State Department of Fish and Game.

Raymond M. and Rousset F. (1995) GENEPOP (Version1.2): Population genetics software for exact tests and ecumenicism. *Journal of Heredity* 86, 248–249.

Rousset F. and Raymond M. (1995) Testing heterozygote excess and deficiency. *Genetics* 140, 1413–1419.

Sambrook J., Fritsch E. F. and Maniatis T. (1989) Molecular cloning: a laboratory manual. (2nd ed). Plainview: Cold Spring Harbor Laboratory Press.

Slate J., Marshall T. and Pemberton J. (2000) A Retrospective assessment of the accuracy of the paternity inference program CERVUS. *Molecular Ecology* 9, 801–808.

Smith R. N. (1995) Accurate size comparison of short tandem repeat alleles amplified by PCR. *Biotechniques* 18, 122–128.

Stone R. T., Pulido J. C., Duyk G. M., Kappes S. M., Keele J. W., & Beattie C. W. (1995) A small-insert bovine genomic library highly enriched for microsatellite repeat sequences. *Mammalian Genome* 6, 714–724.

Thomson J. A., Pilotti V., Stevens P., Ayres K. L., & Debenham P. G. (1999) Validation of short tandem repeat analysis for the investigation of cases of disputed paternity. *Forensic Science International* 100, 1–16.

TABLE 4

Appendix A

BM1225

| Size[1] | Repeat[2] | Std. Dev.[3] | AI | CSP | EIP | EIW | FN | GC | HM | JA | MBS | MX | NBR | WBNP | WC | YNP | ABR | HHP | AN | HE | HO | SH | TLH |
|---|---|---|---|---|---|---|---|---|---|---|---|---|---|---|---|---|---|---|---|---|---|---|---|
| 219 | | 0.02 | | | | | | | | | | | | | | | | | | | | 0.125 | 0.077 |
| 215 | | 0.10 | | | | | | | | | | | | | | | | | | | | 0.042 | |
| 117 | | na | | | | | | | | | | | | | | | | | | | | | 0.018 |
| 119 | | 0.20 | | | | | | | | | | | | | | | | | 0.120 | | | | 0.169 |
| 241 | 16 | 0.24 | 0.136 | 0.149 | 0.354 | 0.063 | 0.196 | 0.527 | 0.119 | 0.465 | 0.025 | 0.529 | 0.024 | 0.167 | 0.161 | 0.457 | 0.049 | 0.105 | 0.120 | 0.633 | 0.375 | 0.208 | 0.116 |
| 243 | | 0.15 | | 0.191 | 0.125 | | 0.478 | | | | 0.138 | | 0.431 | 0.028 | 0.122 | | 0.459 | 0.663 | 0.759 | 0.567 | 0.331 | 0.112 | 0.115 |
| 145 | | 0.16 | | | 0.063 | 0.011 | | | | | | | | | 0.003 | 0.003 | 0.008 | | | | | | |
| 147 | 18 | 0.16 | | | 0.063 | 0.083 | | | | | 0.050 | 0.043 | 0.014 | 0.083 | 0.046 | 0.007 | 0.015 | 0.023 | | | | | |
| 249 | | 0.28 | 0.015 | 0.068 | 0.063 | | | | | | | | 0.111 | 0.028 | | | 0.060 | | | 0.031 | 0.292 | 0.083 | 0.038 |
| 251 | 20 | 0.01 | | | 0.042 | | | 0.031 | | | | | | | | | | | | 0.063 | | | 0.038 |
| 253 | | 0.27 | 0.127 | 0.243 | 0.125 | 0.183 | 0.043 | 0.061 | 0.313 | 0.145 | 0.650 | 0.114 | 0.056 | 0.472 | 0.201 | 0.199 | 0.146 | 0.047 | | | | | |
| 255 | 22 | 0.05 | | | 0.061 | | | | 0.143 | | | | | | 0.001 | | | | | | | | | |
| 259 | | 0.38 | | | | 0.042 | | | | | 0.013 | | | | | | | | | | | | | |
| 261 | | na | | | | | | | | | | | | | | | | | | | | | | 0.073 |
| 165 | | 0.21 | 0.052 | 0.081 | | | 0.043 | 0.092 | 0.024 | | | 0.071 | | 0.028 | 0.105 | | 0.119 | | | | | | | |
| 267 | | na | | | | 0.021 | | | | | | | | | | | | | | | | | | |
| 269 | 28 | 0.23 | 0.022 | 0.021 | | 0.167 | 0.217 | 0.490 | 0.143 | 0.382 | 0.142 | 0.129 | 0.236 | 0.167 | 0.059 | 0.019 | 0.116 | 0.128 | | | | | |
| 271 | 30 | 0.24 | | 0.135 | 0.083 | | | | 0.143 | | 0.013 | | | | 0.076 | 0.245 | 0.030 | 0.023 | | | | | |
| 273 | | 0.10 | 0.001 | | | | 0.022 | | 0.043 | | | 0.014 | 0.125 | 0.028 | | | | 0.012 | | | | | | |
| 275 | 11 | 0.14 | | | 0.021 | 0.021 | | | 0.043 | | | | | | | | | | | | | | | |
| | | Het[4] | 0.580 | 0.806 | 0.827 | 0.615 | 0.689 | 0.614 | 0.818 | 0.615 | 0.546 | 0.656 | 0.732 | 0.721 | 0.803 | 0.708 | 0.736 | 0.516 | 0.398 | 0.472 | 0.677 | 0.633 | 0.793 |
| | | PIC[5] | 0.354 | 0.773 | 0.801 | 0.589 | 0.636 | 0.560 | 0.786 | 0.529 | 0.512 | 0.610 | 0.690 | 0.680 | 0.775 | 0.652 | 0.708 | 0.503 | 0.361 | 0.357 | 0.589 | 0.697 | 0.249 |
| | | PEI[6] | 0.075 | 0.433 | 0.491 | 0.230 | 0.270 | 0.227 | 0.456 | 0.186 | 0.167 | 0.147 | 0.329 | 0.319 | 0.439 | 0.283 | 0.354 | 0.160 | 0.078 | 0.103 | 0.220 | 0.234 | 0.406 |
| | | PE2[7] | 0.210 | 0.611 | 0.664 | 0.412 | 0.444 | 0.383 | 0.633 | 0.319 | 0.318 | 0.422 | 0.509 | 0.503 | 0.616 | 0.457 | 0.540 | 0.331 | 0.201 | 0.176 | 0.368 | 0.409 | 0.584 |

BM1106

| Size | Repeat | Std. Dev. | AI | CSP | EIP | EIW | FN | GC | HM | JA | MBS | MX | NBR | WBNP | WC | YNP | ABR | HHP | AN | HE | HO | SH | TLH |
|---|---|---|---|---|---|---|---|---|---|---|---|---|---|---|---|---|---|---|---|---|---|---|---|
| 232 | 11 | 0.14 | 0.246 | 0.054 | 0.104 | 0.560 | 0.146 | 0.150 | 0.100 | 0.136 | 0.112 | 0.200 | 0.316 | 0.267 | 0.174 | 0.076 | 0.060 | 0.302 | | | | | 0.035 |
| 234 | | 0.11 | | | | | | | | | 0.013 | | | | | | | | | | | | | |
| 236 | | na | | | | | | | | | | | | | | | | | | | | | | |
| 238 | 14 | 0.12 | 0.614 | 0.527 | 0.771 | 0.540 | 0.667 | 0.700 | 0.900 | 0.803 | 0.663 | 0.786 | 0.658 | 0.595 | 0.510 | 0.747 | 0.112 | 0.372 | 0.119 | | 0.083 | 0.042 | |
| 240 | | na | | | | | | | | | 0.013 | | | | | | | | | | | 0.375 | 0.451 | |
| 242 | | 0.01 | | | | | | | | | | | | | 0.003 | | | | | 0.031 | | | | 0.071 |
| 244 | | 0.06 | | 0.095 | | | | | | | | | | | 0.016 | | 0.004 | | | 0.063 | | | | 0.115 |
| 246 | 16 | na | | | | | | | | | | | 0.016 | | | | | | | | | | | 0.018 |
| 249 | | 0.15 | 0.082 | 0.176 | 0.104 | 0.080 | 0.188 | 0.010 | | 0.061 | 0.013 | | | 0.048 | | 0.036 | 0.015 | 0.023 | 0.491 | 0.406 | 0.042 | 0.042 | 0.346 |
| 250 | 20 | 0.10 | 0.037 | 0.149 | 0.011 | 0.020 | | 0.140 | | | 0.150 | 0.016 | 0.470 | 0.071 | 0.016 | 0.146 | 0.090 | 0.035 | 0.167 | 0.500 | 0.167 | 0.292 | 0.346 |
| 252 | | 0.18 | | | | | | | | | 0.018 | | 0.380 | 0.024 | 0.016 | 0.025 | 0.060 | 0.167 | 0.083 | | 0.113 | 0.234 | |
| 254 | | 0.16 | | | | | | | | | | | | | 0.261 | | | | 0.120 | | | 0.125 | 0.035 |
| 256 | | | | | | | | | | | | | | | | | | | | | | | | |
| | | Het | 0.661 | 0.662 | 0.388 | 0.578 | 0.504 | 0.470 | 0.182 | 0.335 | 0.527 | 0.345 | 0.470 | 0.576 | 0.642 | 0.332 | 0.189 | 0.705 | 0.683 | 0.589 | 0.727 | 0.699 | 0.751 |
| | | PIC | 0.519 | 0.619 | 0.357 | 0.491 | 0.448 | 0.425 | 0.164 | 0.109 | 0.491 | 0.293 | 0.380 | 0.514 | 0.583 | 0.308 | 0.370 | 0.634 | 0.614 | 0.494 | 0.662 | 0.636 | 0.696 |
| | | PEI | 0.222 | 0.253 | 0.076 | 0.167 | 0.125 | 0.111 | 0.016 | 0.055 | 0.152 | 0.059 | 0.109 | 0.175 | 0.223 | 0.055 | 0.081 | 0.265 | 0.267 | 0.173 | 0.295 | 0.274 | 0.339 |

TABLE 4-continued

Appendix A

| Size | Repeat | PE2 Std. Dev. | AI | CSP | EIP | EIW | FN | GC | HM | JA | MBS | MX | NBR | WBNP | WC | YNP | ABR | HHP | AN | HE | HO | SH | TLH |
|---|---|---|---|---|---|---|---|---|---|---|---|---|---|---|---|---|---|---|---|---|---|---|---|
| | | 0.371 | 0.431 | 0.209 | 0.293 | 0.265 | 0.255 | 0.082 | 0.169 | 0.316 | 0.152 | 0.202 | 0.326 | 0.383 | 0.175 | 0.224 | 0.430 | 0.469 | 0.295 | 0.466 | 0.445 | 0.511 |
| | | | | | | | | | | | BM17132 | | | | | | | | | | | | |
| 75 | | na | | | | | | | | | | | | | | | | | | | | | |
| 79 | | 0.05 | | | | | | | | | | | | | | | | | | | | | |
| 81 | 13 | 0.06 | | | | | | | | | | | | | | | | | | | | | |
| 81 | | 0.10 | 0.881 | 0.230 | 0.085 | 0.104 | 0.152 | 0.561 | | 0.015 | 0.275 | 0.371 | 0.092 | 0.238 | | | | | 0.039 | | | 0.050 | |
| 85 | 15 | 0.09 | 0.022 | 0.446 | 0.417 | 0.146 | 0.152 | 0.102 | 0.476 | 0.061 | 0.097 | 0.143 | 0.474 | 0.024 | 0.431 | 0.062 | 0.435 | 0.395 | 0.031 | 0.251 | 0.167 | 0.050 | 0.211 |
| 87 | | 0.09 | 0.082 | 0.311 | 0.250 | 0.616 | 0.543 | 0.245 | 0.214 | | 0.125 | 0.314 | 0.434 | 0.452 | 0.336 | 0.373 | 0.069 | 0.301 | 0.226 | 0.467 | 0.375 | 0.100 | 0.077 |
| 89 | 17 | 0.09 | 0.007 | 0.014 | 0.250 | 0.063 | 0.152 | 0.092 | | 0.924 | 0.200 | 0.071 | | 0.214 | 0.234 | 0.142 | 0.155 | 0.253 | 0.208 | 0.063 | 0.542 | 0.200 | 0.346 |
| 91 | | na | | | | | | | 0.310 | | | | | | | 0.214 | 0.141 | 0.070 | | | | 0.010 | 0.011 |
| 93 | | 0.05 | | | | | | | | | | | | | | 0.029 | | | | | | | |
| 95 | 20 | na | 0.007 | | | | | | | | 0.025 | | | | | | | | 0.009 | | 0.042 | | 0.018 |
| 97 | | na | | | | | | | | | | | | | | | | | 0.009 | | | | |
| 99 | | 0.11 | | | | | | | | | | | | | | 0.130 | | | 0.066 | 0.155 | 0.250 | 0.550 | |
| 101 | | 0.04 | | | | | | | | | | | | | | | | | 0.311 | 0.031 | | | 0.231 |
| 103 | | 0.05 | | | | | | | | | | | | | | | | | 0.123 | | | | |
| | Het | 0.47 | 0.218 | 0.656 | 0.701 | 0.551 | 0.642 | 0.609 | 0.639 | 0.143 | 0.768 | 0.704 | 0.582 | 0.675 | 0.649 | 0.776 | 0.663 | 0.702 | 0.395 | 0.671 | 0.765 | 0.650 | 0.315 |
| | PIC | 0.07 | 0.206 | 0.582 | 0.619 | 0.513 | 0.691 | 0.554 | 0.558 | 0.135 | 0.725 | 0.641 | 0.437 | 0.636 | 0.573 | 0.739 | 0.597 | 0.615 | 0.757 | 0.605 | 0.712 | 0.604 | 0.125 |
| | PE1 | na | 0.024 | 0.217 | 0.267 | 0.165 | 0.221 | 0.199 | 0.199 | 0.010 | 0.566 | 0.269 | 0.167 | 0.268 | 0.209 | 0.384 | 0.236 | 0.264 | 0.410 | 0.245 | 0.551 | 0.243 | 0.564 |
| | PE2 | 0.45 | 0.111 | 0.368 | 0.434 | 0.316 | 0.197 | 0.360 | 0.346 | 0.070 | 0.544 | 0.434 | 0.284 | 0.438 | 0.355 | 0.564 | 0.392 | 0.428 | 0.598 | 0.410 | 0.530 | 0.421 | 0.542 |
| | | | | | | | | | | | | BM1905 | | | | | | | | | | | |
| Size | Repeat | Std. Dev. | AI | CSP | EIP | EIW | FN | GC | HM | JA | MBS | MX | NBR | WBNP | WC | YNP | ABR | HHP | AN | HE | HO | SH | TLH |
| 110 | | 0.15 | | | | 0.063 | | | | | 0.013 | | | 0.024 | | | | | | | | | 0.038 |
| 173 | 12 | 0.11 | 0.022 | 0.236 | 0.260 | 0.896 | 0.870 | 0.170 | 0.403 | 0.109 | 0.769 | 0.314 | 0.171 | 0.619 | 0.172 | 0.064 | 0.496 | 0.116 | | | | | |
| 124 | | 0.09 | | | | | | | | | | | | | | | | | | | | | | 0.058 |
| 176 | 14 | 0.08 | 0.246 | 0.709 | 0.604 | | 0.130 | 0.720 | 0.592 | 0.469 | 0.141 | 0.557 | 0.579 | 0.310 | 0.311 | 0.795 | 0.158 | 0.779 | 0.019 | 0.063 | | | 0.423 |
| 178 | | 0.27 | | | | | | | | | | | | | | | | | | 0.102 | 0.219 | 0.331 | 0.125 | 0.215 |
| 180 | 16 | 0.24 | 0.007 | | 0.146 | 0.021 | | | | | | | 0.026 | | | 0.141 | 0.010 | | 0.148 | 0.039 | | 0.292 | |
| 182 | | na | 0.030 | | | 0.021 | | 0.990 | | 0.422 | 0.038 | 0.071 | 0.224 | 0.018 | | | 0.116 | 0.105 | 0.019 | 0.123 | 0.125 | 0.042 | 0.038 |
| 184 | 18 | na | 0.694 | 0.028 | | | | | | | 0.038 | | | | | | | | 0.602 | 0.563 | 0.208 | 0.083 | 0.269 |
| 186 | | 0.10 | | | | | | | | | | | | | | | | | | | | 0.333 | 0.333 | |
| 188 | | | | 0.028 | | | | | | | | | | | | | | | | | | 0.042 | |
| 192 | | | | | | | | | | | | | | | 0.017 | | | | 0.028 | | | | |
| 194 | | | | | | | | | | | | 0.057 | | | | | | | 0.083 | | | 0.083 | 0.017 |
| 198 | 25 | | | | | | | | | | | | | | | | | | | | | | |
| | Het | | 0.458 | 0.444 | 0.557 | 0.195 | 0.229 | 0.443 | 0.489 | 0.595 | 0.168 | 0.587 | 0.589 | 0.524 | 0.316 | 0.318 | 0.613 | 0.173 | 0.603 | 0.625 | 0.114 | 0.783 | 0.739 |
| | PIC | | 0.396 | 0.383 | 0.487 | 0.185 | 0.201 | 0.397 | 0.366 | 0.503 | 0.358 | 0.514 | 0.528 | 0.442 | 0.275 | 0.790 | 0.637 | 0.339 | 0.367 | 0.570 | 0.663 | 0.338 | 0.683 |
| | PE1 | | 0.106 | 0.099 | 0.152 | 0.019 | 0.026 | 0.093 | 0.116 | 0.174 | 0.073 | 0.178 | 0.178 | 0.137 | 0.050 | 0.050 | 0.194 | 0.068 | 0.209 | 0.212 | 0.291 | 0.189 | 0.323 |
| | PE2 | | 0.226 | 0.216 | 0.292 | 0.100 | 0.101 | 0.230 | 0.183 | 0.297 | 0.211 | 0.319 | 0.331 | 0.256 | 0.143 | 0.160 | 0.314 | 0.192 | 0.388 | 0.380 | 0.464 | 0.565 | 0.506 |
| | | | | | | | | | | | | BM2113 | | | | | | | | | | | |
| Size | Repeat | Std. Dev. | AI | CSP | EIP | EIW | FN | GC | HM | JA | MBS | MX | NBR | WBNP | WC | YNP | ABR | HHP | AN | HE | HO | SH | TLH |
| 125 | | 0.03 | | | | | | | | | | 0.071 | | | | | | | | | | | |

TABLE 4-continued

Appendix A

| | | AI | CSP | EIP | EIW | FN | GC | HM | JA | MBS | MX | NBR | WBNP | WC | YNP | ABR | HHP | AN | HE | HO | SH | TLH |
|---|---|---|---|---|---|---|---|---|---|---|---|---|---|---|---|---|---|---|---|---|---|---|
| 127 | | | 0.041 | 0.047 | | 0.063 | | | | 0.125 | | | 0.048 | 0.076 | | 0.049 | 0.093 | 0.120 | 0.031 | 0.203 | 0.208 | 0.077 |
| 129 | 15 | 0.761 | 0.122 | 0.331 | 0.720 | 0.146 | 0.360 | 0.548 | | 0.463 | 0.143 | 0.539 | 0.571 | 0.257 | 0.247 | 0.340 | 0.229 | | | 0.125 | | 0.231 |
| 131 | 17 | | | | | | | | | | | | | 0.097 | | | | | | | | | 0.038 |
| 133 | | | 0.324 | | | | | | | 0.013 | 0.014 | 0.013 | | 0.220 | 0.101 | 0.136 | 0.058 | 0.185 | 0.031 | 0.083 | 0.292 | 0.154 |
| 135 | | | 0.011 | | | | 0.300 | 0.024 | | 0.013 | 0.057 | | | 0.112 | | | | 0.370 | 0.459 | 0.500 | 0.042 | 0.023 |
| 137 | | | | | | | | | | | | | | | | | | 0.019 | 0.031 | 0.083 | 0.133 | 0.385 |
| 139 | | | | | | | | | | | | | | | | | | 0.185 | 0.406 | | 0.083 | |
| 141 | | | | | | 0.375 | 0.190 | | | 0.087 | 0.457 | | 0.143 | 0.003 | | 0.239 | 0.430 | 0.120 | 0.031 | | 0.042 | 0.018 |
| 143 | 22 | 0.231 | 0.324 | 0.354 | 0.120 | 0.146 | 0.150 | 0.429 | 0.939 | 0.300 | 0.071 | 0.263 | 0.890 | 0.164 | 0.595 | 0.149 | 0.116 | | | | | |
| 145 | | | 0.081 | | 0.050 | | | | 0.061 | | | | 0.029 | 0.131 | | 0.011 | 0.023 | | | | | |
| 147 | | | 0.054 | 0.271 | 0.100 | | | | | | | 0.171 | 0.024 | 0.010 | 0.057 | 0.075 | | | | | | |
| 153 | 27 | 0.007 | 0.014 | | | 0.271 | | | | | 0.186 | 0.013 | | | | | | | | | | |
| | | | | | | | | | | | | | | | | | | | | | | |
| | Het | 0.363 | 0.761 | 0.696 | 0.458 | 0.747 | 0.725 | 0.522 | 0.115 | 0.677 | 0.728 | 0.614 | 0.621 | 0.820 | 0.569 | 0.781 | 0.719 | 0.772 | 0.621 | 0.692 | 0.766 | 0.775 |
| | PIC | 0.306 | 0.728 | 0.625 | 0.424 | 0.698 | 0.671 | 0.405 | 0.107 | 0.619 | 0.691 | 0.548 | 0.572 | 0.792 | 0.510 | 0.747 | 0.668 | 0.731 | 0.516 | 0.638 | 0.709 | 0.728 |
| | PE1 | 0.061 | 0.377 | 0.253 | 0.103 | 0.332 | 0.297 | 0.135 | 0.027 | 0.256 | 0.331 | 0.194 | 0.214 | 0.461 | 0.169 | 0.196 | 0.305 | 0.373 | 0.102 | 0.271 | 0.147 | 0.376 |
| | PE2 | 0.156 | 0.555 | 0.412 | 0.261 | 0.510 | 0.470 | 0.215 | 0.054 | 0.423 | 0.515 | 0.347 | 0.393 | 0.616 | 0.320 | 0.376 | 0.481 | 0.554 | 0.139 | 0.450 | 0.524 | 0.536 |

BM4440

| Size | Repeat | AI | CSP | EIP | EIW | FN | GC | HM | JA | MBS | MX | NBR | WBNP | WC | YNP | ABR | HHP | AN | HE | HO | SH | TLH |
|---|---|---|---|---|---|---|---|---|---|---|---|---|---|---|---|---|---|---|---|---|---|---|
| 121 | | 0.007 | 0.027 | 0.063 | 0.146 | 0.167 | 0.120 | | | 0.038 | 0.113 | 0.066 | 0.025 | | | 0.032 | 0.035 | 0.185 | 0.031 | | | 0.016 |
| 123 | 15 | 0.015 | 0.230 | 0.104 | 0.271 | 0.104 | 0.030 | 0.405 | 1.030 | 0.188 | 0.147 | 0.197 | 0.125 | 0.342 | | 0.566 | 0.244 | 296 | 0.344 | 0.458 | 0.457 | 0.269 |
| 125 | 11 | 0.716 | 0.027 | 0.375 | 0.188 | 0.229 | 0.590 | 0.071 | | 0.150 | 0.118 | 0.429 | 0.250 | 0.049 | 0.566 | 0.146 | 0.198 | | 0.053 | | | 0.154 |
| 127 | | 0.246 | 0.581 | 0.208 | 0.333 | 0.333 | 0.190 | 0.405 | | 0.439 | 0.279 | 0.039 | 0.150 | 0.560 | 0.266 | 0.299 | 0.477 | | | | | |
| 129 | 19 | 0.001 | 0.103 | 0.219 | 0.063 | 0.146 | 0.070 | 0.119 | | 0.175 | 0.162 | 0.276 | 0.400 | 0.026 | 0.120 | 0.131 | 0.023 | 0.111 | 0.469 | 0.157 | 0.083 | 0.016 |
| 131 | | 0.003 | 0.023 | 0.021 | | 0.021 | | | | 0.013 | | | 0.050 | | 0.016 | | | 0.324 | | | 0.167 | 0.115 |
| 133 | | | | | | | | | | | | | | | | | | 0.019 | | | | |
| 137 | | | | | | | | | | | | | | | | | | 0.019 | | | 0.167 | |
| 139 | | | | | | | | | | | | | | | | | | | | | 0.053 | |
| 141 | | | | | | | | | | | | | | | | | | | | | | |
| 143 | 24 | | | | | | | | | | | 0.176 | | | | 0.030 | 0.023 | 0.037 | 0.031 | 0.208 | 0.55 | 0.038 |
| 145 | | | | | | | | | | | | | | | | | | | 0.063 | 0.125 | | 0.231 |
| 141 | | | | | | | | | | | | | | 0.016 | 0.166 | | | 0.009 | 0.031 | 0.042 | | 0.154 |
| 149 | | | | | | | | | | | | | | | | | | | | | | |
| | | | | | | | | | | | | | | | | | | | | | | |
| | Het | 0.427 | 0.600 | 0.756 | 0.763 | 0.384 | 0.599 | 0.661 | 0.000 | 0.721 | 0.821 | 0.706 | 0.746 | 0.561 | 0.630 | 0.770 | 0.680 | 0.765 | 0.663 | 0.716 | 0.766 | 0.827 |
| | PIC | 0.163 | 0.549 | 0.709 | 0.713 | 0.752 | 0.555 | 0.587 | 0.000 | 0.619 | 0.790 | 0.651 | 0.697 | 0.482 | 0.566 | 0.731 | 0.621 | 0.720 | 0.594 | 0.639 | 0.719 | 0.784 |
| | PE1 | 0.092 | 0.198 | 0.342 | 0.350 | 0.387 | 0.199 | 0.230 | 0.000 | 0.312 | 0.456 | 0.283 | 0.334 | 0.163 | 0.210 | 0.374 | 0.355 | 0.361 | 0.241 | 0.291 | 0.361 | 0.449 |
| | PE2 | 0.199 | 0.362 | 0.526 | 0.328 | 0.567 | 0.369 | 0.183 | 0.000 | 0.491 | 0.612 | 0.454 | 0.512 | 0.289 | 0.365 | 0.553 | 0.423 | 0.539 | 0.400 | 0.469 | 0.546 | 0.626 |

BM720

| Size | Repeat | AI | CSP | EIP | EIW | FN | GC | HM | JA | MBS | MX | NBR | WBNP | WC | YNP | ABR | HHP | AN | HE | HO | SH | TLH |
|---|---|---|---|---|---|---|---|---|---|---|---|---|---|---|---|---|---|---|---|---|---|---|
| 203 | 9 | | 0.054 | | | 0.174 | | | | | 0.015 | | | | | 0.004 | 0.116 | | | | | |
| 209 | | | | | | | | | | | | | | | | | | | | | | 0.115 |
| 213 | | | 0.095 | | | | 0.052 | 0.167 | | | 0.029 | 0.091 | | 0.224 | 0.166 | 0.097 | 0.023 | 0.009 | 0.031 | 0.042 | 0.083 | 0.115 |
| 215 | | | | | | | | | | | | | | | | | | 0.500 | | 0.083 | 0.333 | 0.135 |
| 217 | | | | | | | | | | | | | | | | | | | 0.125 | | | 0.035 |
| 219 | | | | | | | | | | | | | | | | | | | | 0.167 | | |
| 221 | | | | | | | | | | | | | | | | | | | | | | |

TABLE 4-continued

Appendix A

| Size | Repeat | Std. Dev. | AI | CSP | EIP | EIW | FN | GC | HM | JA | MBS | MX | NBR | WBNP | WC | YNP | ABR | HHP | AN | HE | HO | SH | TLH |
|---|---|---|---|---|---|---|---|---|---|---|---|---|---|---|---|---|---|---|---|---|---|---|---|
| 223 | 19 | | 0.022 | 0.189 | 0.083 | 0.152 | 0.022 | 0.521 | 0.024 | 0.128 | 0.105 | 0.124 | 0.131 | 0.211 | 0.089 | 0.142 | 0.239 | 0.093 | 0.009 | | | | |
| 225 | | | | 0.143 | | 0.152 | | | | | 0.092 | 0.015 | | 0.132 | 0.193 | 0.003 | 0.067 | 0.213 | | | | | |
| 227 | 21 | | 0.061 | 0.054 | 0.438 | 0.543 | 0.239 | 0.052 | 0.524 | | 0.474 | 0.294 | 0.081 | 0.474 | 0.102 | 0.267 | 0.164 | 0.070 | 0.157 | 0.156 | 0.083 | 0.031 | 0.038 |
| 229 | 22 | | 0.455 | 0.297 | 0.375 | 0.087 | 0.391 | 0.229 | 0.286 | 0.094 | 0.250 | 0.324 | 0.622 | 0.184 | 0.257 | 0.307 | 0.429 | 0.384 | 0.157 | 0.313 | 0.167 | 0.041 | 0.154 |
| 231 | 23 | | 0.453 | 0.054 | 0.104 | 0.065 | 0.174 | 0.146 | | 0.578 | 0.039 | | 0.081 | | 0.132 | 0.047 | | 0.070 | 0.281 | 0.031 | 0.167 | 0.081 | 0.423 |
| 233 | | | | 0.014 | | | | | | | | | | | | 0.068 | | 0.012 | 0.037 | | | | |
| 235 | | | | | | | | | | | | | | | | | | | 0.019 | | 0.125 | 0.083 | |
| 237 | | | | | | | | | | | | | | | | | | | 0.037 | | | 0.292 | |
| 239 | | | | | | | | | | | | | | | | | | | | | | | |
| | | Het | 0.511 | 0.104 | 0.657 | 0.654 | 0.717 | 0.653 | 0.623 | 0.554 | 0.692 | 0.708 | 0.580 | 0.689 | 0.812 | 0.793 | 0.721 | 0.775 | 0.693 | 0.790 | 0.876 | 0.791 | 0.769 |
| | | PIC | 0.491 | 0.771 | 0.534 | 0.610 | 0.634 | 0.636 | 0.551 | 0.470 | 0.644 | 0.644 | 0.545 | 0.632 | 0.782 | 0.737 | 0.676 | 0.736 | 0.652 | 0.744 | 0.841 | 0.743 | 0.727 |
| | | PE1 | 0.172 | 0.433 | 0.229 | 0.245 | 0.313 | 0.240 | 0.197 | 0.151 | 0.279 | 0.273 | 0.190 | 0.260 | 0.446 | 0.409 | 0.510 | 0.388 | 0.287 | 0.394 | 0.549 | 0.197 | 0.375 |
| | | PE2 | 0.291 | 0.610 | 0.382 | 0.424 | 0.489 | 0.411 | 0.147 | 0.274 | 0.455 | 0.436 | 0.367 | 0.433 | 0.621 | 0.588 | 0.538 | 0.568 | 0.469 | 0.572 | 0.711 | 0.575 | 0.563 |

BM51117

| Size | Repeat | Std. Dev. | AI | CSP | EIP | EIW | FN | GC | HM | JA | MBS | MX | NBR | WBNP | WC | YNP | ABR | HHP | AN | HE | HO | SH | TLH |
|---|---|---|---|---|---|---|---|---|---|---|---|---|---|---|---|---|---|---|---|---|---|---|---|
| 87 | | | | | | | | | | | | | | | | | | | 0.039 | | 0.250 | 0.083 | |
| 89 | 13 | 0.03 | 0.903 | 0.432 | 0.342 | 0.680 | | 0.370 | 0.214 | 0.106 | 0.500 | 0.486 | 0.176 | 0.550 | 0.470 | 0.253 | 0.379 | 0.163 | | 0.156 | 0.042 | 0.048 | 0.269 |
| 91 | | 0.10 | 0.073 | 0.351 | 0.487 | 0.240 | 0.500 | 0.160 | 0.214 | 0.894 | 0.397 | 0.229 | 0.095 | 0.225 | 0.421 | 0.228 | 0.383 | 0.538 | 0.120 | 0.375 | 0.292 | 0.208 | 0.385 |
| 93 | | 0.07 | 0.015 | 0.203 | 0.042 | 0.080 | 0.646 | 0.430 | 0.571 | | 0.103 | 0.243 | 0.551 | 0.175 | 0.103 | 0.519 | 0.197 | 0.263 | 0.528 | 0.469 | 0.115 | 0.667 | 0.037 |
| 95 | | 0.17 | 0.007 | | | | 0.208 | | | | | | 0.027 | | | | | | 0.106 | | | | 0.037 |
| 97 | | 0.12 | | | | | | | | | | | 0.122 | | | | | | | | | | 0.038 |
| 99 | | 0.06 | | 0.014 | | | | 0.040 | | | | 0.043 | | 0.050 | | | 0.030 | 0.038 | 0.037 | | 0.042 | | 0.192 |
| 101 | | 0.01 | | | | | | | | | | | | | | | | | | | | | 0.038 |
| 103 | | 0.06 | | | | | | | | | | | | | | | | | | | | | |
| | | na | | | | | | | | | | | | | | | | | | | | | |
| | | Het | 0.179 | 0.653 | 0.537 | 0.478 | 0.641 | 0.654 | 0.389 | 0.191 | 0.585 | 0.656 | 0.618 | 0.672 | 0.593 | 0.617 | 0.673 | 0.622 | 0.618 | 0.625 | 0.723 | 0.514 | 0.745 |
| | | PIC | 0.169 | 0.577 | 0.428 | 0.414 | 0.370 | 0.387 | 0.517 | 0.172 | 0.494 | 0.591 | 0.568 | 0.560 | 0.505 | 0.545 | 0.605 | 0.555 | 0.548 | 0.536 | 0.634 | 0.456 | 0.691 |
| | | PE1 | 0.016 | 0.215 | 0.141 | 0.112 | 0.209 | 0.224 | 0.169 | 0.018 | 0.169 | 0.226 | 0.208 | 0.201 | 0.177 | 0.188 | 0.240 | 0.199 | 0.199 | 0.189 | 0.284 | 0.133 | 0.127 |
| | | PE2 | 0.089 | 0.363 | 0.235 | 0.257 | 0.362 | 0.375 | 0.385 | 0.056 | 0.290 | 0.385 | 0.382 | 0.362 | 0.101 | 0.334 | 0.356 | 0.154 | 0.349 | 0.329 | 0.452 | 0.278 | 0.508 |

BM51172

| Size | Repeat | Std. Dev. | AI | CSP | EIP | EIW | FN | GC | HM | JA | MBS | MX | NBR | WBNP | WC | YNP | ABR | HHP | AN | HE | HO | SH | TLH |
|---|---|---|---|---|---|---|---|---|---|---|---|---|---|---|---|---|---|---|---|---|---|---|---|
| 86 | | | | | | | | | | | | 0.029 | | | | | | | | | | | 0.015 |
| 88 | 13 | 0.10 | 0.157 | 0.108 | 0.292 | 0.040 | 0.083 | 0.290 | 0.095 | 0.015 | 0.038 | 0.214 | 0.176 | 0.095 | 0.392 | 0.015 | 0.030 | 0.122 | | 0.500 | 0.500 | 0.308 | |
| 90 | 14 | 0.11 | 0.067 | 0.473 | 0.333 | 0.760 | 0.646 | 0.490 | 0.313 | 0.015 | 0.738 | 0.686 | 0.392 | 0.595 | 0.294 | 0.627 | 0.207 | 0.451 | 0.500 | 0.406 | 0.161 | 0.173 | 0.131 |
| 92 | 15 | 0.13 | | | | | 0.208 | 0.020 | | | | 0.014 | 0.162 | | 0.003 | | 0.481 | | 0.333 | | 0.250 | 0.125 | 0.038 |
| 94 | | 0.09 | | | | | | | | | | | | | | 0.006 | 0.004 | | 0.028 | 0.094 | 0.083 | 0.042 | 0.077 |
| 96 | | 0.09 | | | | | | | | | | | | | | | | | 0.139 | | | | 0.115 |
| 98 | | 0.10 | | | | 0.200 | | | 0.071 | | | | | 0.024 | | | | 0.085 | | | | | |
| 100 | | na | 0.067 | 0.297 | 0.208 | | 0.063 | 0.050 | | 0.015 | 0.016 | 0.057 | 0.149 | 0.095 | 0.162 | 0.022 | 0.139 | 0.183 | | | | | |
| 102 | 20 | 0.10 | | | 0.167 | | | 0.060 | | 0.333 | 0.138 | | 0.122 | 0.190 | 0.003 | 0.203 | 0.083 | 0.159 | | | | | |
| 104 | | 0.12 | 0.709 | 0.122 | | | | 0.090 | | 0.591 | | | | | 0.145 | 0.117 | 0.053 | | | | | | |
| | | 0.11 | | | | | | | | | | | | | | | | | | | | | |
| | | Het | 0.466 | 0.666 | 0.740 | 0.385 | 0.534 | 0.665 | 0.295 | 0.541 | 0.421 | 0.483 | 0.758 | 0.398 | 0.717 | 0.546 | 0.695 | 0.724 | 0.625 | 0.585 | 0.667 | 0.415 | 0.453 |
| | | PIC | 0.430 | 0.605 | 0.683 | 0.333 | 0.481 | 0.611 | 0.272 | 0.457 | 0.377 | 0.432 | 0.717 | 0.550 | 0.665 | 0.495 | 0.655 | 0.678 | 0.569 | 0.486 | 0.599 | 0.412 | 0.420 |
| | | PE1 | 0.114 | 0.241 | 0.309 | 0.073 | 0.148 | 0.252 | 0.041 | 0.148 | 0.090 | 0.120 | 0.354 | 0.195 | 0.295 | 0.158 | 0.291 | 0.311 | 0.199 | 0.166 | 0.234 | 0.114 | 0.107 |
| | | PE2 | 0.263 | 0.404 | 0.483 | 0.189 | 0.101 | 0.420 | 0.150 | 0.208 | 0.218 | 0.259 | 0.336 | 0.365 | 0.467 | 0.312 | 0.429 | 0.495 | 0.344 | 0.231 | 0.400 | 0.264 | 0.261 |

TABLE 4-continued

Appendix A

BM51862

| Size | Repeat | Std. Dev. | AI | CSP | EIP | EIW | FN | GC | HM | JA | MBS | MX | NBR | WBNP | WC | YNP | ABR | HHP | AN | HE | HO | SH | TLH |
|---|---|---|---|---|---|---|---|---|---|---|---|---|---|---|---|---|---|---|---|---|---|---|---|
| 142 | 9 | 0.00 | | | | | | | | | | | | | | | | | | | | | |
| 144 | | 0.06 | | | | | | | | | | | | | | | | | | | | | |
| 148 | | na | | | | | | | | | | | | | | | | | | | | | |
| 152 | | na | | | | | | | | | | | | | | | | | | | | | |
| 154 | | 0.10 | 0.343 | 0.311 | 0.208 | 0.180 | 0.375 | 0.200 | 0.119 | | 0.385 | 0.300 | 0.081 | 0.262 | 0.361 | 0.352 | 0.222 | 0.238 | | | | | |
| 156 | | 0.06 | | | | 0.160 | | 0.060 | | | | 0.143 | | 0.024 | | | 0.019 | | 0.278 | | | 0.300 | 0.035 |
| 158 | 17 | 0.05 | | | | | | | | | | | | | | | | | | | | | |
| 160 | | 0.07 | 0.127 | 0.392 | 0.042 | | 0.025 | 0.250 | 0.071 | | 0.013 | 0.051 | 0.284 | 0.048 | 0.248 | 0.017 | 0.049 | 0.107 | 0.389 | 0.188 | 0.083 | 0.087 | 0.131 |
| 162 | 19 | 0.07 | 0.007 | 0.135 | 0.208 | 0.100 | 0.125 | 0.030 | | | 0.218 | 0.200 | | 0.024 | 0.238 | 0.145 | 0.203 | 0.107 | 0.009 | | | 0.042 | 0.154 |
| 164 | 10 | 0.05 | 0.015 | 0.034 | 0.042 | | 0.050 | 0.720 | 0.071 | 0.641 | 0.017 | 0.129 | 0.054 | 0.119 | 0.030 | 0.062 | 0.038 | 0.119 | | | 0.208 | 0.041 | 0.033 |
| 166 | | 0.09 | 0.485 | 0.027 | 0.104 | 0.440 | | 0.060 | 0.357 | | 0.051 | 0.014 | 0.189 | 0.048 | 0.010 | 0.079 | 0.079 | 0.036 | | 0.063 | | 0.203 | 0.077 |
| 168 | 23 | 0.09 | | 0.027 | 0.042 | 0.120 | 0.250 | 0.050 | 0.048 | 0.141 | 0.141 | 0.043 | 0.054 | 0.119 | 0.036 | 0.162 | 0.038 | 0.036 | 0.157 | 0.061 | | 0.041 | 0.192 |
| 170 | | 0.09 | 0.022 | 0.014 | 0.271 | | 0.175 | 0.120 | 0.167 | | 0.315 | 0.114 | 0.338 | 0.262 | 0.060 | 0.173 | 0.053 | 0.250 | 0.009 | 0.695 | 0.560 | 0.033 | 0.192 |
| 172 | | 0.11 | | | 0.083 | | | 0.010 | 0.167 | 0.219 | | | | 0.048 | 0.017 | 0.110 | 0.177 | 0.107 | 0.009 | | 0.161 | 0.042 | 0.038 |
| 174 | | na | | | | | | | | | | | | | | | | | 0.009 | | | | |
| 190 | | na | | | | | | | | | | | | | | 0.041 | | | | | 0.043 | | |
| 193 | | 0.05 | | | | | | | | | | | | | | | | | 0.139 | | | | 0.018 |
| Het | | | 0.632 | 0.703 | 0.825 | 0.731 | 0.757 | 0.828 | 0.800 | 0.526 | 0.768 | 0.821 | 0.762 | 0.834 | 0.741 | 0.793 | 0.842 | 0.840 | 0.734 | 0.492 | 0.634 | 0.702 | 0.354 |
| PIC | | | 0.563 | 0.649 | 0.793 | 0.631 | 0.709 | 0.801 | 0.764 | 0.465 | 0.731 | 0.791 | 0.719 | 0.803 | 0.704 | 0.764 | 0.319 | 0.808 | 0.683 | 0.443 | 0.627 | 0.654 | 0.317 |
| PE1 | | | 0.212 | 0.283 | 0.466 | 0.321 | 0.346 | 0.480 | 0.424 | 0.136 | 0.378 | 0.463 | 0.260 | 0.481 | 0.341 | 0.425 | 0.310 | 0.492 | 0.316 | 0.123 | 0.260 | 0.294 | 0.507 |
| PE2 | | | 0.361 | 0.457 | 0.610 | 0.503 | 0.525 | 0.653 | 0.604 | 0.276 | 0.559 | 0.618 | 0.538 | 0.660 | 0.519 | 0.605 | 0.679 | 0.664 | 0.491 | 0.271 | 0.435 | 0.476 | 0.676 |

BM52639

| Size | Repeat | Std. Dev. | AI | CSP | EIP | EIW | FN | GC | HM | JA | MBS | MX | NBR | WBNP | WC | YNP | ABR | HHP | AN | HE | HO | SH | TLH |
|---|---|---|---|---|---|---|---|---|---|---|---|---|---|---|---|---|---|---|---|---|---|---|---|
| 156 | 14 | na | | | | | | | | | | | | | | | | | | | | | 0.018 |
| 164 | | 0.12 | 0.015 | | 0.370 | 0.380 | | 0.400 | | 0.424 | 0.063 | 0.015 | 0.081 | 0.013 | 0.253 | 0.194 | 0.197 | 0.125 | 0.358 | 0.021 | 0.175 | 0.083 | 0.162 |
| 165 | | 0.17 | 0.239 | 0.135 | 0.304 | 0.340 | 0.313 | 0.040 | 0.143 | | 0.050 | 0.265 | 0.203 | 0.167 | 0.291 | 0.389 | 0.261 | 0.150 | | 0.094 | 0.417 | 0.250 | 0.192 |
| 168 | 17 | 0.03 | 0.664 | 0.324 | 0.217 | 0.340 | 0.146 | 0.230 | 0.381 | 0.061 | 0.482 | 0.309 | 0.149 | 0.286 | 0.345 | 0.391 | 0.130 | 0.425 | 0.216 | 0.405 | 0.083 | 0.125 | 0.017 |
| 170 | | 0.13 | 0.022 | 0.338 | 0.022 | 0.060 | 0.125 | 0.160 | 0.476 | | 0.362 | 0.221 | 0.459 | 0.262 | 0.007 | | 0.023 | 0.088 | 0.028 | 0.313 | 0.167 | | | 0.192 |
| 172 | 19 | 0.12 | 0.015 | | | 0.060 | 0.183 | 0.140 | | 0.132 | 0.175 | 0.118 | 0.260 | 0.024 | 0.103 | | 0.129 | 0.035 | | 0.156 | 0.125 | 0.011 | |
| 174 | | 0.09 | 0.045 | 0.027 | | 0.020 | 0.138 | 0.030 | | | 0.138 | 0.044 | 0.081 | 0.071 | | | 0.061 | 0.175 | 0.066 | | 0.031 | 0.175 | |
| 176 | | 0.11 | | 0.031 | | | 0.042 | | | | | | | 0.119 | | | | | 0.301 | | | | | 0.038 |
| 178 | 21 | 0.22 | | | | | | | | | | | | | | | | | | | | | | |
| 180 | | 0.10 | | | | | | | | | | | | | | | | | | | | | | |
| 184 | | na | | | | | | | | | | | | 0.024 | | 0.025 | | | 0.039 | | | | | |
| 186 | | 0.08 | | 0.095 | 0.037 | | | | | 0.364 | | 0.029 | 0.027 | | | | | | | | | | | |
| 190 | | na | | | | | | | | | | | | | | | | | | | | | | |
| Het | | | 0.501 | 0.751 | 0.723 | 0.720 | 0.802 | 0.743 | 0.615 | 0.666 | 0.752 | 0.775 | 0.717 | 0.809 | 0.727 | 0.652 | 0.766 | 0.751 | 0.726 | 0.719 | 0.770 | 0.777 | 0.728 |
| PIC | | | 0.446 | 0.106 | 0.664 | 0.663 | 0.363 | 0.701 | 0.527 | 0.597 | 0.715 | 0.732 | 0.676 | 0.773 | 0.674 | 0.375 | 0.726 | 0.709 | 0.669 | 0.652 | 0.724 | 0.727 | 0.655 |
| PE1 | | | 0.131 | 0.346 | 0.294 | 0.302 | 0.416 | 0.338 | 0.195 | 0.236 | 0.356 | 0.375 | 0.312 | 0.433 | 0.102 | 0.214 | 0.365 | 0.349 | 0.300 | 0.285 | 0.369 | 0.111 | 0.330 |
| PE2 | | | 0.269 | 0.523 | 0.464 | 0.474 | 0.595 | 0.517 | 0.316 | 0.391 | 0.578 | 0.553 | 0.491 | 0.610 | 0.474 | 0.361 | 0.544 | 0.552 | 0.470 | 0.456 | 0.531 | 0.553 | 0.479 |

BM5410

| Size | Repeat | Std. Dev. | AI | CSP | EIP | EIW | FN | GC | HM | JA | MBS | MX | NBR | WBNP | WC | YNP | ABR | HHP | AN | HE | HO | SH | TLH |
|---|---|---|---|---|---|---|---|---|---|---|---|---|---|---|---|---|---|---|---|---|---|---|---|

TABLE 4-continued

Appendix A

| Size | AI | CSP | EIP | EIW | FN | GC | HM | JA | MBS | MX | NBR | WBNP | WC | YNP | ABR | HHP | AN | HE | HO | SH | TLH |
|---|---|---|---|---|---|---|---|---|---|---|---|---|---|---|---|---|---|---|---|---|---|
| 81 | 0.036 | 0.635 | 0.333 | 0.020 | 0.600 | 0.406 | 0.667 | 0.106 | 0.013 | 0.400 | 0.486 | 0.071 | 0.566 | 0.471 | 0.003 | 0.547 | 0.083 | 0.094 | 0.273 | 0.413 | 0.077 |
| 83 | 0.262 | 0.081 | 0.042 | 0.080 | | 0.156 | | | 0.183 | 0.243 | 0.041 | 0.095 | 0.158 | | 0.447 | 0.015 | | 0.031 | | 0.042 | 0.269 |
| 85 | | 0.014 | | | | | 0.095 | 0.030 | 0.138 | | | 0.048 | | | 0.056 | | | | | 0.042 | |
| 87 | | | | | 0.045 | 0.229 | 0.024 | 0.470 | 0.013 | 0.329 | 0.284 | 0.024 | 0.276 | 0.013 | 0.346 | 0.384 | 0.019 | | | | |
| 89 | 0.638 | 0.257 | 0.604 | 0.840 | 0.455 | | | | 0.538 | | 0.081 | 0.667 | | 0.252 | | | 0.296 | | 0.111 | 0.125 | 0.500 |
| 91 | | | | | | | | | 0.013 | | | | | | | | 0.028 | | 0.056 | | 0.038 |
| 93 | | 0.014 | | | | 0.083 | | 0.194 | 0.087 | 0.029 | 0.014 | 0.024 | | 0.003 | 0.094 | 0.012 | 0.083 | | 0.333 | 0.042 | |
| 95 | 0.015 | | 0.021 | 0.050 | | 0.125 | | | 0.013 | | 0.091 | 0.071 | | 0.258 | 0.041 | 0.023 | | | | | |
| 97 | | | | | | | | | | | | | | | 0.008 | | | | | | |
| 99 | | | | | | | | | | | | | | | | | 0.065 | 0.003 | 0.056 | 0.161 | 0.077 |
| 103 | | | | | | | | | | | | | | | | | 0.287 | 0.531 | 0.111 | 0.361 | 0.038 |
| 105 | | | | | | | 0.214 | | | | | | | | | | 0.056 | 0.186 | 0.056 | | |
| 107 | | | | | | | | | | | | | | | | | | 0.091 | | | |
| 109 | | | | | | | | | | | | | | | | | 0.083 | | | | |

| Repeat | Het | PIC | PE1 | PE2 | | | | | | | | | | | | | | | | | |
|---|---|---|---|---|---|---|---|---|---|---|---|---|---|---|---|---|---|---|---|---|---|
| | Std. Dev. | | | | | | | | | | | | | | | | | | | | |
| 12 | 0.10 | | | | | | | | | | | | | | | | | | | | |
| | 0.06 | | | | | | | | | | | | | | | | | | | | |
| | 0.11 | | | | | | | | | | | | | | | | | | | | |
| 15 | 0.25 | | | | | | | | | | | | | | | | | | | | |
| | 0.09 | | | | | | | | | | | | | | | | | | | | |
| | 0.29 | | | | | | | | | | | | | | | | | | | | |
| 17 | 0.19 | | | | | | | | | | | | | | | | | | | | |
| | 0.09 | | | | | | | | | | | | | | | | | | | | |
| 19 | 0.24 | | | | | | | | | | | | | | | | | | | | |
| | 0.09 | | | | | | | | | | | | | | | | | | | | |
| | 0.03 | | | | | | | | | | | | | | | | | | | | |
| | 0.03 | | | | | | | | | | | | | | | | | | | | |
| | na | | | | | | | | | | | | | | | | | | | | |
| | 0.09 | | | | | | | | | | | | | | | | | | | | |

| | Het | 0.519 | 0.327 | 0.527 | 0.287 | 0.543 | 0.739 | 0.506 | 0.617 | 0.653 | 0.617 | 0.670 | 0.519 | 0.581 | 0.670 | 0.669 | 0.559 | 0.803 | 0.671 | 0.800 | 0.766 | 0.676 |
| | PIC | 0.454 | 0.464 | 0.459 | 0.269 | 0.436 | 0.695 | 0.430 | 0.534 | 0.611 | 0.608 | 0.616 | 0.512 | 0.510 | 0.601 | 0.610 | 0.453 | 0.775 | 0.626 | 0.747 | 0.719 | 0.617 |
| | PE1 | 0.136 | 0.142 | 0.138 | 0.041 | 0.147 | 0.131 | 0.129 | 0.194 | 0.247 | 0.237 | 0.256 | 0.162 | 0.167 | 0.293 | 0.253 | 0.156 | 0.445 | 0.262 | 0.401 | 0.364 | 0.257 |
| | PE2 | 0.269 | 0.279 | 0.251 | 0.152 | 0.241 | 0.511 | 0.271 | 0.311 | 0.425 | 0.392 | 0.424 | 0.395 | 0.388 | 0.383 | 0.415 | 0.269 | 0.621 | 0.444 | 0.580 | 0.347 | 0.428 |

BM5510

| Size | AI | CSP | EIP | EIW | FN | GC | HM | JA | MBS | MX | NBR | WBNP | WC | YNP | ABR | HHP | AN | HE | HO | SH | TLH |
|---|---|---|---|---|---|---|---|---|---|---|---|---|---|---|---|---|---|---|---|---|---|
| 82 | | | | | | | | | | | | | | | | | | | | | |
| 84 | | | | | | | | | | | | | | | | | | | 0.045 | 0.040 | |
| 88 | | | | | | | | | | | | | | | | | | 0.094 | | | 0.077 |
| 90 | | | | | | | | | | | | | | | | | | | | | |
| 91 | 0.969 | 0.471 | 0.130 | 0.625 | 0.229 | 0.310 | 0.214 | 0.303 | 0.015 | 0.386 | 0.399 | 0.452 | 0.682 | 0.365 | 0.395 | 0.114 | 0.370 | 0.544 | 0.409 | 0.333 | 0.423 |
| 92 | 0.008 | 0.382 | 0.500 | 0.195 | 0.188 | 0.370 | 0.143 | 0.697 | 0.637 | 0.214 | 0.292 | 0.239 | 0.197 | 0.331 | 0.301 | 0.267 | 0.065 | | | 0.042 | 0.154 |
| 12A | | 0.074 | 0.043 | 0.104 | 0.229 | 0.100 | 0.310 | | 0.097 | 0.229 | 0.069 | 0.119 | 0.105 | 0.036 | 0.105 | 0.256 | | | | | |
| 13A | 0.023 | 0.074 | 0.326 | 0.083 | 0.354 | 0.220 | 0.333 | | 0.150 | 0.171 | 0.250 | 0.190 | 0.095 | 0.197 | 0.199 | 0.163 | | | | | |
| 14 | | | | | | | | | 0.050 | | | | | | | | | | | | |
| 95 | | | | | | | | | | | | | | | | | 0.009 | 0.039 | 0.091 | 0.333 | 0.192 |
| 96 | | | | | | | | | | | | | | | | | 0.037 | | 0.045 | 0.042 | 0.038 |
| 98 | | | | | | | | | | | | | | | | | | | | | 0.071 |
| 100 | | | | | | | | | | | | | | | | | | 0.031 | 0.045 | | |
| 102 | | | | | | | | | | | | | | | | | 0.472 | 0.903 | 0.273 | 0.125 | 0.035 |
| 104 | | | | | | | | | | | | | | | | | 0.046 | | 0.091 | 0.063 | |
| 106 | | | | | | | | | | | | | | | | | | | | | |
| 108 | | | | | | | | | | | | | | | | | | | | | |

| | Het | 0.060 | 0.626 | 0.632 | 0.562 | 0.742 | 0.712 | 0.736 | 0.426 | 0.559 | 0.729 | 0.701 | 0.697 | 0.580 | 0.671 | 0.706 | 0.747 | 0.638 | 0.631 | 0.753 | 0.766 | 0.760 |
| | PIC | 0.059 | 0.549 | 0.538 | 0.514 | 0.686 | 0.614 | 0.676 | 0.133 | 0.323 | 0.675 | 0.638 | 0.618 | 0.510 | 0.606 | 0.649 | 0.619 | 0.365 | 0.554 | 0.699 | 0.713 | 0.715 |
| | PE1 | 0.002 | 0.205 | 0.208 | 0.167 | 0.312 | 0.281 | 0.308 | 0.089 | 0.174 | 0.301 | 0.266 | 0.266 | 0.167 | 0.241 | 0.231 | 0.314 | 0.219 | 0.208 | 0.345 | 0.339 | 0.160 |
| | PE2 | 0.030 | 0.347 | 0.356 | 0.329 | 0.486 | 0.450 | 0.475 | 0.167 | 0.346 | 0.475 | 0.431 | 0.437 | 0.308 | 0.401 | 0.446 | 0.488 | 0.363 | 0.356 | 0.522 | 0.315 | 0.542 |

BM5523

| Size | AI | CSP | EIP | EIW | FN | GC | HM | JA | MBS | MX | NBR | WBNP | WC | YNP | ABR | HHP | AN | HE | HO | SH | TLH |
|---|---|---|---|---|---|---|---|---|---|---|---|---|---|---|---|---|---|---|---|---|---|
| 159 | 0.119 | | 0.021 | | | 0.110 | | | | 0.014 | 0.029 | 0.095 | 0.010 | 0.047 | 0.038 | | | | | | |
| 163 | 0.033 | 0.135 | 0.146 | 0.040 | 0.053 | 0.110 | 0.024 | | 0.141 | 0.186 | 0.103 | 0.071 | | 0.019 | 0.011 | | | | | | |
| 165 | | | 0.208 | | | | | | | 0.041 | 0.092 | | | | | | | | | | |

| Repeat | | | | | | | | | | | | | | | | | | | | | |
|---|---|---|---|---|---|---|---|---|---|---|---|---|---|---|---|---|---|---|---|---|---|
| 11 | 0.05 | | | | | | | | | | | | | | | | | | | | |
| 13 | 0.06 | | | | | | | | | | | | | | | | | | | | |
| 14 | 0.13 | | | | | | | | | | | | | | | | | | | | |

TABLE 4-continued

Appendix A

| Size | | | | | | | | | | | | | | | | | | | | | | | | |
|---|---|---|---|---|---|---|---|---|---|---|---|---|---|---|---|---|---|---|---|---|---|---|---|---|
| | 0.037 | 0.054 | 0.063 | 0.240 | 0.184 | 0.120 | | 0.331 | 0.167 | 0.129 | 0.013 | 0.333 | 0.010 | 0.023 | 0.143 | 0.021 | 0.170 | | 0.125 | 0.042 | | | | |
| 167 | | | | | | | | | | | | | | | | | | | 0.042 | | | | | |
| 169 | | | | | | | | | | | | | | | | | | | | | | | | |
| 171 | | | | | | | | | | | | | | | | | | | | | | | | |
| 173 | 0.419 | 0.294 | 0.229 | 0.140 | 0.342 | 0.400 | 0.543 | 0.045 | 0.106 | 0.280 | 0.551 | 0.262 | 0.247 | 0.259 | 0.485 | 0.500 | 0.056 | | | 0.208 | | 0.083 | | 0.018 |
| 175 | 0.188 | 0.150 | 0.271 | 0.060 | 0.289 | 0.160 | 0.256 | 0.676 | 0.167 | 0.214 | 0.158 | 0.119 | 0.160 | 0.463 | 0.139 | 0.384 | 0.009 | | | | | | | 0.077 |
| 177 | | 0.297 | 0.063 | 0.320 | 0.132 | 0.100 | 0.143 | 0.045 | 0.218 | 0.129 | | 0.119 | 0.573 | 0.180 | 0.184 | 0.081 | 0.259 0.031 | | | | | | | 0.108 |
| 179 | | | | | | | | | | | | | | | | | 0.028 0.438 | | | 0.500 | 0.167 | | | 0.115 |
| 181 | | | | | | | | | | | | | | | 0.012 | 0.407 0.418 | | | 0.083 | 0.206 | | | 0.077 |
| 183 | | | | | | | | | | | | | | | | | 0.102 | | | 0.042 | | | | 0.269 |
| 185 | | | | | | | | | | | | | | | | | | | | | | | | 0.115 |
| 187 | | | | | | | | | | | | | | | | | 0.009 | | | | | | | |
| 189 | | | | | | | | | | | | | | | | | 0.009 | | | | | | | |

| | Het | 0.660 | 0.762 | 0.610 | 0.727 | 0.135 | 0.770 | 0.605 | 0.558 | 0.787 | 0.809 | 0.648 | 0.787 | 0.587 | 0.674 | 0.892 | 0.602 | 0.745 | 0.621 | 0.695 | 0.684 | 0.308 |
|---|---|---|---|---|---|---|---|---|---|---|---|---|---|---|---|---|---|---|---|---|---|---|
| | PIC | 0.594 | 0.716 | 0.772 | 0.668 | 0.702 | 0.738 | 0.553 | 0.476 | 0.743 | 0.715 | 0.611 | 0.746 | 0.525 | 0.620 | 0.650 | 0.516 | 0.701 | 0.514 | 0.643 | 0.621 | 0.763 |
| | PE1 | 0.218 | 0.350 | 0.431 | 0.298 | 0.316 | 0.386 | 0.195 | 0.138 | 0.791 | 0.433 | 0.247 | 0.196 | 0.177 | 0.256 | 0.283 | 0.185 | 0.114 | 0.199 | 0.279 | 0.160 | 0.424 |
| | PE2 | 0.393 | 0.527 | 0.608 | 0.466 | 0.513 | 0.570 | 0.132 | 0.284 | 0.571 | 0.611 | 0.429 | 0.575 | 0.326 | 0.424 | 0.456 | 0.316 | 0.523 | 0.774 | 0.439 | 0.435 | 0.602 |

RM372

| Size | Repeat | Std. Dev. | AI | CSP | EIP | EIW | FN | GC | HM | JA | MBS | MX | NBR | WBNP | WC | YNP | ABR | HHP | AN | HE | HO | SH | TLH |
|---|---|---|---|---|---|---|---|---|---|---|---|---|---|---|---|---|---|---|---|---|---|---|---|
| 114 | 9 | 0.17 | | 0.041 | | | 0.021 | | | | | | | | | | | 0.023 | | | | | |
| 116 | | 0.04 | | | | | | | | | 0.103 | | | 0.071 | 0.030 | 0.020 | 0.015 | | | 0.063 | | | 0.192 |
| 118 | 11 | 0.01 | | 0.365 | 0.152 | | 0.229 | | 0.167 | | 0.038 | 0.071 | 0.043 | 0.048 | 0.293 | 0.534 | 0.135 | 0.244 | | | | | |
| 122 | | na | | | | | | | | | | | | | | | | | | | | | | |
| 126 | | 0.34 | | | | | | | | | | | | | | | | | 0.151 | 0.061 | 0.136 | 0.167 | 0.038 |
| 128 | | 0.22 | 0.412 | 0.108 | 0.457 | 0.217 | 0.146 | 0.638 | 0.222 | 0.091 | 0.051 | 0.086 | 0.029 | 0.143 | 0.140 | 0.106 | 0.113 | 0.116 | 0.150 | 0.375 | 0.545 | 0.411 | 0.077 |
| 130 | 17 | 0.10 | 0.008 | 0.122 | | 0.587 | 0.031 | 0.018 | | 0.121 | 0.531 | 0.586 | 0.329 | 0.524 | 0.260 | 0.137 | 0.338 | 0.031 | 0.208 | 0.250 | 0.091 | 0.161 | 0.108 |
| 132 | | 0.09 | | | | 0.087 | | | | | 0.115 | | | 0.071 | 0.020 | | 0.004 | 0.015 | 0.094 | 0.074 | | 0.041 | 0.018 |
| 134 | 19 | 0.14 | 0.164 | 0.149 | 0.391 | 0.022 | 0.271 | 0.260 | 0.611 | 0.788 | 0.126 | 0.729 | 0.443 | 0.143 | 0.127 | 0.373 | 0.256 | 0.302 | 0.170 | 0.156 | 0.227 | 0.154 |
| 136 | | 0.09 | 0.414 | 0.135 | | 0.360 | 0.250 | 0.100 | | | 0.013 | 0.029 | | | 0.080 | 0.022 | 0.132 | 0.151 | 0.047 | | | 0.205 | 0.192 |
| 138 | | 0.54 | | 0.081 | | | | | | | | | 0.157 | | 0.050 | | 0.008 | 0.047 | | | | | |

| | Het | 0.633 | 0.797 | 0.622 | 0.599 | 0.791 | 0.528 | 0.557 | 0.359 | 0.656 | 0.596 | 0.673 | 0.680 | 0.803 | 0.757 | 0.774 | 0.811 | 0.793 | 0.763 | 0.639 | 0.741 | 0.315 |
|---|---|---|---|---|---|---|---|---|---|---|---|---|---|---|---|---|---|---|---|---|---|---|
| | PIC | 0.555 | 0.767 | 0.335 | 0.548 | 0.743 | 0.462 | 0.489 | 0.328 | 0.623 | 0.545 | 0.610 | 0.641 | 0.773 | 0.712 | 0.737 | 0.776 | 0.754 | 0.721 | 0.574 | 0.684 | 0.778 |
| | PE1 | 0.201 | 0.429 | 0.189 | 0.195 | 0.391 | 0.140 | 0.151 | 0.064 | 0.260 | 0.194 | 0.247 | 0.277 | 0.437 | 0.149 | 0.383 | 0.440 | 0.404 | 0.363 | 0.213 | 0.915 | 0.430 |
| | PE2 | 0.341 | 0.609 | 0.324 | 0.360 | 0.572 | 0.175 | 0.294 | 0.185 | 0.446 | 0.357 | 0.405 | 0.462 | 0.614 | 0.526 | 0.562 | 0.613 | 0.584 | 0.543 | 0.379 | 0.494 | 0.601 |

[1]Allele size (does not include non-template adenine added to 3' terminus by Taq polymerase)
[2]Number of repeats present in the sequenced bison allele.
[3]Standard deviation of called size assigned by Genescan software
[4]Expected heterozygosity
[5]Polymorphic information content
[6]Probability of excluding a putative parent when a confirmed parent's genotypes are unavailable.
[7]Probability of excluding a putative parent when a confirmed parent's genotypes are known.

We claim:

1. A method of determining parentage of a North American bison or domestic cattle offspring comprising:
   i) determining the alleles present in the offspring for selected microsatellite loci;
   ii) determining the alleles present in sampled potential parents of the offspring for the same selected microsatellite loci;
   iii) determining the likelihood that any potential parent is the actual parent of the offspring based upon the presence or absence of an allele for each of the selected loci in the offspring that is present in the potential parent;
   wherein the selected loci comprise BM1225, BM1706, BM17132, BM1905, BM2113, BM4440, BM720, BMS1862, BMS410, BMS510, BMS527, RM372, BMS1172, BMS2639, BM3628 and BMS2325.

2. The method of claim 1, wherein the selected loci consist of BM1225, BM1706, BM17132, BM1905, BM2113, BM4440, BM720, BMS 1862, BMS410, BMS510, BMS527, RM372, BMS1172, BMS2639, BM3628 and BMS2325.

* * * * *